United States Patent [19]
Latta et al.

[11] Patent Number: 5,187,261
[45] Date of Patent: * Feb. 16, 1993

[54] PROCESS FOR THE PREPARATION OF MATURE HUMAN SERUM ALBUMIN

[75] Inventors: Martine Latta, Paris; Jean-Francois Mayaux, Fontenay aux Roses, both of France; Paolo Sarmientos, Milano, Italy

[73] Assignee: Genetica, Joinville le Pont, France

[*] Notice: The portion of the term of this patent subsequent to Apr. 3, 2007 has been disclaimed.

[21] Appl. No.: 653,195

[22] Filed: Feb. 8, 1991

Related U.S. Application Data

[62] Division of Ser. No. 16,651, Dec. 19, 1987, Pat. No. 5,100,784.

[30] Foreign Application Priority Data

Feb. 21, 1986 [FR] France .................. 86 02379

[51] Int. Cl.$^5$ .................. C07K 15/02; C07K 15/06
[52] U.S. Cl. .................. 530/363; 530/364; 435/69.7; 435/69.6
[58] Field of Search .............. 530/363, 364; 435/69.7, 435/69.6

[56] References Cited

U.S. PATENT DOCUMENTS

| | | | |
|---|---|---|---|
| 4,332,892 | 6/1982 | Ptashne | 435/69.1 |
| 4,338,397 | 7/1982 | Gilbert et al. | 435/69.1 |
| 4,468,464 | 8/1984 | Cohen et al. | 435/317 |
| 4,511,502 | 4/1985 | Builder et al. | 435/69.1 |
| 4,551,433 | 11/1985 | DeBoer | 435/253 |
| 4,578,355 | 3/1986 | Rosenberg | 435/317 |
| 4,703,004 | 10/1987 | Hopp et al. | 435/69.7 |
| 4,914,027 | 4/1990 | Knopp et al. | 435/69.6 |

FOREIGN PATENT DOCUMENTS

| | | |
|---|---|---|
| 079739 | 5/1983 | European Pat. Off. |
| 138437 | 4/1985 | European Pat. Off. |
| 200590 | 11/1986 | European Pat. Off. |
| 2140810 | 12/1984 | United Kingdom |

OTHER PUBLICATIONS

Wolfe et al., 1982, J. Biol. Chem. 257(13):7898-7902.
Strauss et al., 1977, Proc. Natl. Acad. Sci. 74(4):1358-1362.
Brennan et al., 1984, Biochimico et Biophysico Acta 802:24-28.
Schumacher et al., 1986 Penicillin G acylase from *E. coli*: unique-gene protection relation, Nuc. Acids Res. 14, 5713-5727.
European Search Report dated Nov. 3, 1986.
Beaucage et al., 1981 Deoxynucleoside phosphoramidites—a new class of key intermediates for deoxypolynucleotide synthesis. Tet. Ltrs. 22, 1859-1862.
Schwarz et al., 1978 Nucleotide sequence of cro, cII and part of the O gene in phage DNA. Nature 272, 410-414.
Rosenberg, et al., 1983, Meth. Enzymol. 101, 123-139.
Oliver et al., 1985, Gene 40, 9-14.
Courtney, et al., 1984, Proc. Nat'l. Acad. Sci. U.S.A. 81, 669-673.
International Biotechnologies, Inc. Catalog, p. 117.
The Embo Journal, vol. 3, No. 6, 1984, pp. 1429-1434, IRL Press Ltd., K. K. Stanley et al., "Construction of a new family of high efficiency bacterial expression vectors: identification of cDNA clones coding . . .".
Laboratory Techniques in Biochemistry and Molecular Biology, "Sequencing of Proteins and Peptides", by G. Allen; pp. 46-57.

*Primary Examiner*—Robert A. Wax
*Assistant Examiner*—Keith C. Furman
*Attorney, Agent, or Firm*—Morgan & Finnegan

[57] ABSTRACT

Mature human serum albumin is produced from a human serum albumin produced by a microbiological route in the form of fused protein ("pseudo-pro-HSA") containing an N-terminal peptide elongation.

4 Claims, 28 Drawing Sheets

STRUCTURE OF THE "PREPRO-HSA"

Met lys trp val thr phe ile ser leu leu phe leu phe ser ser ala tyr ser arg gly val phe arg arg asp ala ...

STRUCTURE OF THE "PREPRO-HSA"

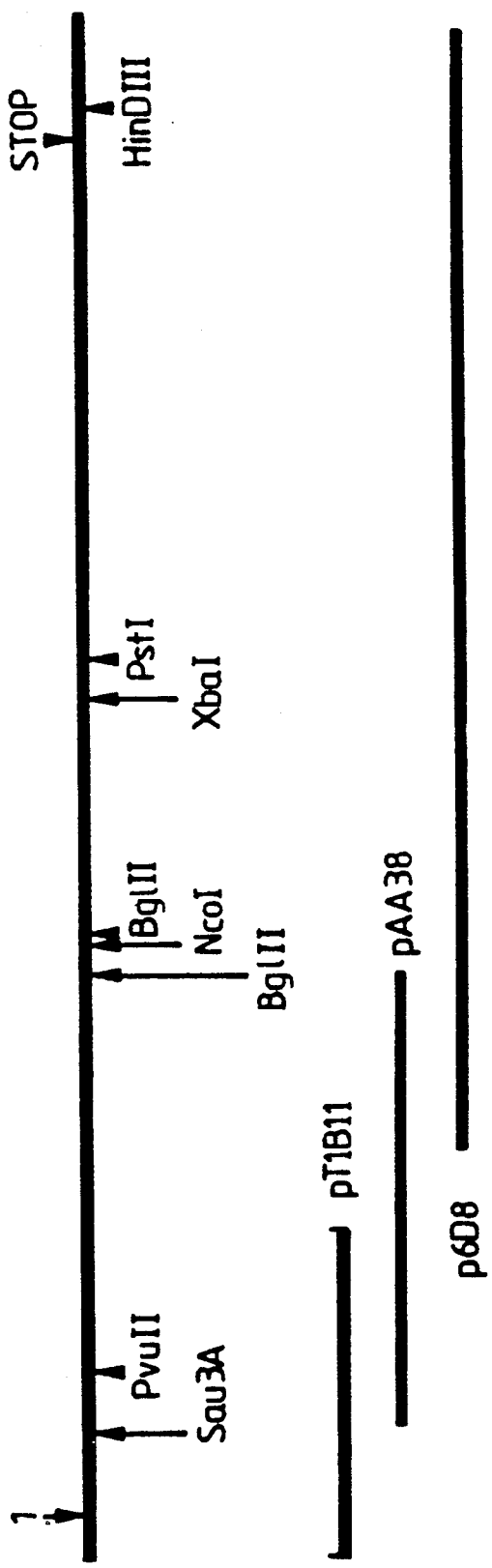

Fig. 3B
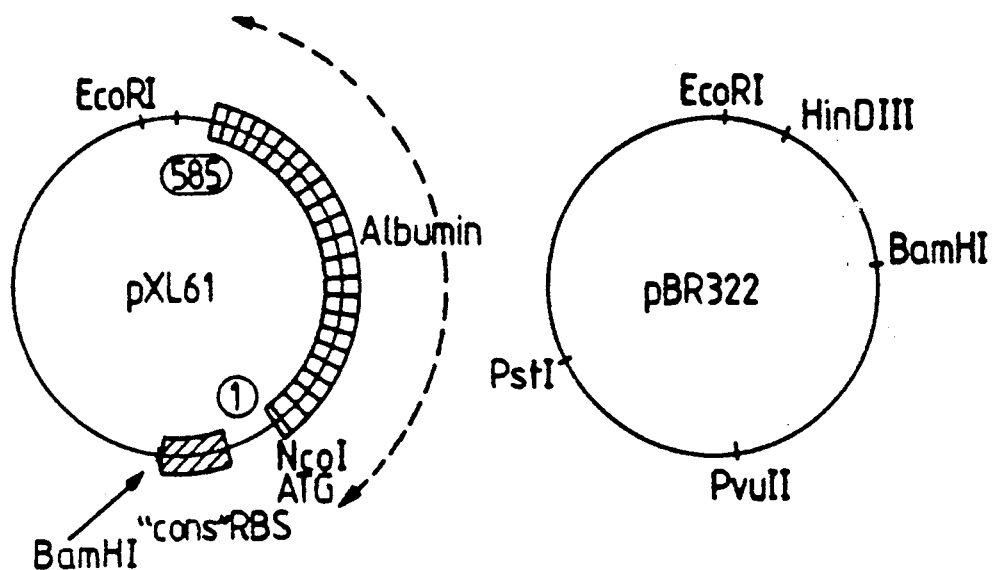
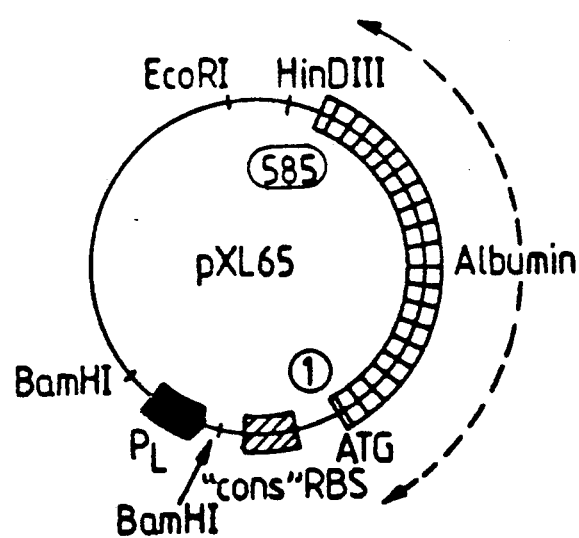

Fig. 4A pxLS3 INSERTION SEQUENCE

```
         10        20        30        40        50        60        70        80
EcoR1
GAATTCCTCACTCATTAGGCACCCCCAGGCTTTACACATTTATGCTTCCGGCTCGTATGTTGTGTGGAATTGTGACCGG 90       100       110       120       130       140       150       160
CTTAAGGAGTGAGTAATCCGTGGGGGTCCGAAAATGTGTAAATACGAAGGCCGAGCATACAACACACCTTAACACTCGCC 170       180       190       200       210       220       230       240
ATAACAATTTCACACAGGAAACAGGAATCCATGATGCACACAAGAGTGAGGTTGCTCATCGGTTTAAAGATTTGGGAGA

TATTGTTAAAGTGTGTCCTTTGTCCTTAGGTACCTACGTGTGTTCTCACTCCAACGAGTAGCCAAATTTCTAAACCCTCT

AGAAAATTTCAAAGCCTTGGTGTTGATTGCCTTTGCTCAGTATCTTCAGCAGTGTCCATTTGAAGATCATGTAAAATTAG

TCTTTTAAAGTTTCGGAACCACAACTAACGGAAACGAGTCATAGAAGTCGTCACAGGTAAACTTCTAGTACATTTAATC
```

Fig. 4B

```
      250       260       270       280       290       300       310       320
TGAATGAAGTAACTGAATTTGCAAAAACATGTGTTGCTGATGAGTCAGCTGAAAATTGTGACAAATCACTTCATACCCTT 330       340       350       360       370       380       390       400
ACTTACTTCATTGACTTAAACGTTTTTGTACACAACGACTACTCAGTCGACTTTTAACACTGTTAGTGAAGTATGGGAA 410       420       430       440       450       460       470       480
TTTGGAGACAAATTATGCACAGTTGCAACTCTTCGTGAAACCTATGGTGAAATGGCTGACTGCTGTGCAAAACAAGAACC 490       500       510       520       530       540       550       560
AAACCTCTGTTAATACGTGTCAACGTTGAGAAGCACTTTGGATACCACTTACCGACTGACGACACGTTTGTTCTTGG

TGAGAGAAATGAATGCTTCTTGCAACACAAAGATGACAATCCAAATCTCCCCGATTGGTGAGACCAGAGGTTGATGTGA

ACTCTCTTACTTACGAAGAACGTTGTGTTTCTACTGTTAGGTTAGAGGGGGCTAACCACTCTGGCTCTCCAACTACACT

TCTGCACTGCTTTCATGACAATGAAGAGACATTTTGAAAAAATACTTATATGAAATTGCCAGAAGACATCCTTACTTT

ACACGTGACGAAAAGTACTGTTACTTCTCTCTGTAAAAACTTTTTTATGAATATACTTTAACGGTCTTCTGTAGGAATGAAA
```

Fig. 4C

```
        570         580         590         600         610         620         630         640
TATGCCCCGGAACTCCTTTCTTTGCTAAAAGGTATAAAGCTGCTTTACAGAATGTTGCCAAGCTGCTGATAAAGCAGC
ATACGGGCCCTTGAGGAAAAGAAACGATTTTCCATATTTCGACGAAAATGTCTTACAACGGTTCGACGACTATTTCGTCG 650         660         670         680         690         700         710         720
CTGCCTGTTGCCAAAGCTCGATGAACTTCGGGATGAAGGGAAGGCTTCGTCTGCCAAACAGAGACTCAAGTGTGCCAGTC
GACGGACAACGGTTTCGAGCTACTTGAAGCCCTACTTCCCTTCCGAAGCAGACGGTTTGTCTCTGAGTTCACACGGTCAG 730         740         750         760         770         780         790         800
TCCAAAAATTTGGAGAAGAGAGCTTTCAAAGCATGGGCAGTAGCTCGCCCTGAGCCAGAGATTTCCCAAAGCTGAGTTTGCA
AGGTTTTTAAACCTCTTTCTCGAAAGTTTCGTACCCGTCATCGAGCGGACTCGGTCTCTAAAGGGTTTCGACTCAAACGT 810         820         830         840         850         860         870         880
GAAGTTCCAAGTTAGTGACAGATCTTACCAAAGTCCACACGGAATGCTGCCATGGAGATCTGCTTGAATGTGCTGATGA
CTTCAAAGGTTCAATCACTGTCTAGAATGGTTTCAGGTGTGCCTTACCACGGTACCTCTAGACGAACTTACACGACTACT
```

Fig. 4D

```
          890       900       910       920       930       940       950       960
CAGGGGGGACCTTGCCAAGTATATCTGTGAAAATCAAGATTCGATCTCCAGTAAACTGAAGGAATGCTGTGAAAAACCTC

GTCCCGCCTGGAACGGTTCATATAGACACTTTTAGTTCTAAGCTAGAGGTCATTTGACTTCCTTACGACACTTTTGGAG
          970       980       990      1000      1010      1020      1030      1040

TGTTGGAAAATCCCACTGCATTGCCGAAGTGGAAAATGATGAGATGCCTGCTGACTTGCCTTCATTAGCGGCTGATTTT

ACAACCTTTTAGGGTGACGTAACGGGCTTCACCTTTTACTACTCCTACGGACGACTGAACGGAAGTAATCGCCGACTAAAA
         1050      1060      1070      1080      1090      1100      1110      1120

GTTGAAAGTAAGGATGTTTGCAAAAACTATGCTGAGGCAAAGGATGTCTTCTTGGGCATGTTTTTGTATGAATATGCAAG

CAACTTTCATTCCTACAAACGTTTTTGATACGACTCCGTTTCCTACAGAAGAACCCGTACAAAAACATACTTATACGTTC
         1130      1140      1150      1160      1170      1180      1190      1200

AAGGCATCCTGATTACTCTGTCGTACTGCTGCCAAGACTTGCCAAGACATATGAAACCACTCTAGAGAAGTGCTGTGCCCG

TTCCGTAGGACTAATGAGACAGCATGACGACGACTCTGAACGGTTCTGTATACTTTGGTGAGATCTCTTCACGACACGGC
```

Fig. 4E

```
       1210      1220      1230      1240      1250      1260      1270      1280
CTGCAGATCCTCATGAATGCTATGCCAAAGTGTTCGATGAATTAAACCTCTTATGGAAGAGCCTCAGAATTTAATCAAA 1290      1300      1310      1320      1330      1340      1350      1360
GACGTCTAGGAGTACTTACGATACGGTTTCACAAGCTACTTAAATTTGGAGAATACCCTTCTCGAGTCTTAAATTAGTTT 1370      1380      1390      1400      1410      1420      1430      1440
CAAAATTGTGAGCTTTTGAGCAGCTTGGAGAGTACAAATTCCAGAATGCGCTATTAGTTCGTTACACCAAGAAGTACC 1450      1460      1470      1480      1490      1500      1510      1520
GTTTAACACTCGAAAAACTCGTCGAACCTCTCATGTTTAAGGTCTTACGCGATAATCAAGCAATGTGGTTCTTTCATGG

CCAAGTGTCAACTCCAACTCTTGTAGAGGTCTCAAGAAACCTAGGAAAAGTGGGCAGCAAATGTTGTAAACATCCTGAAG

GGTTCACAGTTGAGGTTGAGAACATCTCCAGAGTTCTTTGGATCCCTTTTCACCCGTCGTTACAACATTTGTAGGACTTC

CAAAAGAATGCCCTGTGCAGAAGACTATCTATCCGTGGTCCTGAACCAGTTATGTGTTGCATGAGAAACGCCAGTA

GTTTTTCTTACGGGACACGTCTTCTCGATAGATAGGCACCAGGACTTGGTCAATACACACAACGTACTCTTTTGCGGTCAT
```

Fig. 4F

```
         1530      1540      1550      1560      1570      1580      1590      1600
AGTGACAGAGTCACCAAATGCTGCACAGAATCCTTGGTGAACAGGCGACCATGCTTTTCAGCTCTGGAAGTCGATGAAAC 1610      1620      1630      1640      1650      1660      1670      1680
TCACTGTCTCAGTGGTTTACGACGTGTCTCTTAGGAACCACTTGTCCGCTGGTACGAAAAGTCGAGACCTTTCAGCTACTTTG 1610      1620      1630      1640      1650      1660      1670      1680
ATACGTTCCCAAAGAGTTAATGCTGAAACATTCACCTTCCATGCAGATATATGCACACTTTCTGAGAAGGAGAGACAAA 1690      1700      1710      1720      1730      1740      1750      1760
TATGCAAGGGTTTCTCAAATTACGACTTTGTAAGTGGAAGGTACGTCTATATACGTGTGAAAGACTCTTCCTCTCTGTTT 1690      1700      1710      1720      1730      1740      1750      1760
TCAAGAAACAAACTGCACTTGTTGAGCTTGTGAAACACAAGCCCAAGGCAACAAAAGAGCAACTGAAAGCTGTTATGGAT 1770      1780      1790      1800      1810      1820      1830      1840
AGTTCTTTGTTTGACGTGAACAACTCGAACAACACTTTGTGTCCGGTTCCGTTGTTTCTCGTTGACTTTCGACAATACCTA 1770      1780      1790      1800      1810      1820      1830      1840
GATTTCGCAGCTTTTGTAGAGAAGTGCTCCAAGGCTGACGATAAGGAAACCTGCTTTGCCGAGGAGGGTAAAAAACTTGT

CTAAAGCGTCGAAAACATCTCTTCACGACGTTCCGACTGCTATTCCTTTGGACGAAACGGCTCCTCCCATTTTTGAACA
```

Fig. 4G

```
      1850      1860      1870      1880      1890      1900      1910      1920
TGCTGCAAGTCAAGCTGCCTTAGGCTTATAACATCACATTTAAAAGCATCTCAGCCTACCATGAGAATAAGAGAAAGAAA
                      ↑
                    585

ACGACGTTCAGTTCGACGGAATCCGAATATTGTAGTGTAAATTTTCGTAGAGTCGGATGGTACTCTTATTCTCTTTCTTT
      1930      1940      1950      1960      1970      1980      1990      2000

ATGAAGATCAAAAGCTTATTCATTCTGTTTTTCGTTGGTGTAAAAGCCAACACCCTGTCTAAAAAACATAAATT

TACTTCTAGTTTTCGAATAAGTAAGACAAAAAGAAAAAGCAACCACATTTCGGTTGTGGGACAGATTTTTGTATTAA
      2010      2020      2030      2040      2050      2060      2070      2080

TCTTTAATCATTTTAATCATTTGCCTCTTTCTCTGTGCTTCAATTAATAAAAATGCAAAGAATCTAAAAAACCCCC

AGAAATTAGTAAAATTAGTAAAACGGAGAAAAGAGACACGAAGTTAATTATTTTTACCTTTCTTAGATTTTTTGGGGC
      2090      2100      2110      2120      2130      2140      2150      2160
            PstI
CCCCCCCCCCCTGCAGCAATAGCAACAACGTTGCCAAACTATTAACTGGCGAA

GGGGGGGGGGGACGTCGTTATCGTTGTTGCAACGGTTTGATAATTGACCGCTT
```

Fig. 5A

TRANSLATION OF THE HUMAN ALBUMIN GENE INTO pXL53

```
                        125                  140                  155                       170
ATG GAT GCA CAC AAG AGT GAG GTT GCT CAT CGG TTT AAA GAT TTG GGA GAA GAA AAT TTC
MET ASP ALA HIS LYS SER GLU VAL ALA HIS ARG PHE LYS ASP LEU GLY GLU GLU ASN PHE
     ①
                        185                  200                  215                       230
AAA GCC TTG GTG TTG ATT GCC TTT GCT CAG CAG TGT CCA TTT GAA GAT CAT
LYS ALA LEU VAL LEU ILE ALA PHE ALA GLN GLN CYS PRO PHE GLU ASP HIS 245                  260                  275                       290
GTA AAA TTA GTG AAT GAA GTA ACT GAA TTT GCA AAA ACA TGT GTT GCT GAT GAG TCA GCT
VAL LYS LEU VAL ASN GLU VAL THR GLU PHE ALA LYS THR CYS VAL ALA ASP GLU SER ALA 305                  320                  335                       350
GAA AAT TGT GAC AAA TCA CTT TTT GGA GAC AAA TTA TGC ACA GTT GCA ACT
GLU ASN CYS ASP LYS SER LEU PHE GLY ASP LYS LEU CYS THR VAL ALA THR
```

Fig. 5B

```
                    365                   380                    395                          410
CTT CGT GAA ACC TAT GGT GAA ATG GCT GAC TGC TGT GCA AAA CAA GAA CCT GAG AGA AAT
LEU ARG GLU THR TYR GLY GLU MET ALA ASP CYS CYS ALA LYS GLN GLU PRO GLU ARG ASN 425                   440                    455                          470
GAA TGC TTC TTG CAA CAC AAA GAT GAC AAT CCA AAT CTC CCC CGA TTG GTG AGA CCA GAG
GLU CYS PHE LEU GLN HIS LYS ASP ASP ASN PRO ASN LEU PRO ARG LEU VAL ARG PRO GLU 485                   500                    515                          530
GTT GAT GTG ATG TGC ACT GCT TTT CAT GAC AAT GAA GAG ACA TTT TTG AAA AAA TAC TTA
VAL ASP VAL MET CYS THR ALA PHE HIS ASP ASN GLU GLU THR PHE LEU LYS LYS TYR LEU 545                   560                    575                          590
TAT GAA ATT GCC AGA AGA CAT CCT TAC TTT TAT GCC CCG GAA CTC CTT TTC TTT GCT AAA
TYR GLU ILE ALA ARG ARG HIS PRO TYR PHE TYR ALA PRO GLU LEU LEU PHE PHE ALA LYS
```

Fig. 5C

```
                605             620             635             650
AGG TAT AAA GCT GCT TTT ACA GAA TGT TGC CAA GCT GCT GAT AAA GCA GCC TGC CTG TTG
ARG TYR LYS ALA ALA PHE THR GLU CYS CYS GLN ALA ALA ASP LYS ALA ALA CYS LEU LEU 665             680             695             710
CCA AAG CTC GAA CTT CGG GAT GAA GGG AAG GCT TCG TCT GCC AAA CAG AGA CTC AAG
PRO LYS LEU GLU LEU ARG ASP GLU GLY LYS ALA SER SER ALA LYS GLN ARG LEU LYS 725             740             755             770
TGT GCC AGT CTC CAA AAA TTT GGA GAA AGA GCT TTC AAA GCA TGG GCA GTA GCT CGC CTG
CYS ALA SER LEU GLN LYS PHE GLY GLU ARG ALA PHE LYS ALA TRP ALA VAL ALA ARG LEU 785             800             815             830
AGC CAG AGA TTT CCC AAA GCT GAG TTT GCA GAA GTT TCC AAG TTA GTG ACA GAT CTT ACC
SER GLN ARG PHE PRO LYS ALA GLU PHE ALA GLU VAL SER LYS LEU VAL THR ASP LEU THR
```

Fig. 5D

```
                845                860                875                890
AAA GTC CAC ACG GAA TGC TGC CAT GGA GAT CTG CTT GAA TGT GCT GAT GAC AGG GCG GAC
LYS VAL HIS THR GLU CYS CYS HIS GLY ASP LEU LEU GLU CYS ALA ASP ASP ARG ALA ASP 905                920                935                950
CTT GCC AAG TAT ATC TGT GAA AAT CAA GAT TCC ATC TCC AGT AAA CTG AAG GAA TGC TGT
LEU ALA LYS TYR ILE CYS GLU ASN GLN ASP SER ILE SER SER LYS LEU LYS GLU CYS CYS 965                980                995               1010
GAA AAA CCT CTG TTG GAA AAA TCC CAC TGC ATT GCC GAA GTG GAA AAT GAT GAG ATG CCT
GLU LYS PRO LEU LEU GLU LYS SER HIS CYS ILE ALA GLU VAL GLU ASN ASP GLU MET PRO 1025               1040               1055               1070
GCT GAC TTG CCT TCA TTA GCG GCT GAT TTT GTT GAA AGT AAG GAT GTT TGC AAA AAC TAT
ALA ASP LEU PRO SER LEU ALA ALA ASP PHE VAL GLU SER LYS ASP VAL CYS LYS ASN TYR
```

Fig. 5E

```
                1085                    1100                    1115                           1130
GCT GAG GCA AAG GAT GTC TTC TTG GGC ATG TTT TTG TAT GAA TAT GCA AGA AGG CAT CCT
ALA GLU ALA LYS ASP VAL PHE LEU GLY MET PHE LEU TYR GLU TYR ALA ARG ARG HIS PRO 1145                    1160                    1175                           1190
GAT TAC TCT GTC GTA CTG CTG AGA CTT GCC AAG ACA TAT GAA ACC ACT CTA GAG AAG
ASP TYR SER VAL VAL LEU LEU ARG LEU ALA LYS THR TYR GLU THR THR LEU GLU LYS 1205                    1220                    1235                           1250
TGC TGT GCC GCT GCA GAT CCT CAT GAA TGC TAT GCC AAA GTG TTC GAT GAA TTT AAA CCT
CYS CYS ALA ALA ALA ASP PRO HIS GLU CYS TYR ALA LYS VAL PHE ASP GLU PHE LYS PRO 1265                    1280                    1295                           1310
CTT ATG GAA GAG CCT CAG AAT TTA ATC AAA CAA AAT TGT GAG CTT TTT GAG CAG CTT GGA
LEU MET GLU GLU PRO GLN ASN LEU ILE LYS GLN ASN CYS GLU LEU PHE GLU GLN LEU GLY
```

Fig. 5F

```
                    1325                      1340                          1355                        1370
GAG TAC AAA TTC CAG AAT GCG CTA TTA GTT CGT TAC ACC AAG AAA GTA CCC CAA GTG TCA
GLU TYR LYS PHE GLN ASN ALA LEU LEU VAL ARG TYR THR LYS LYS VAL PRO GLN VAL SER 1385                      1400                          1415                        1430
ACT CCA ACT CTT GTA GAG GTC TCA AGA AAC CTA GGA AAA GTG GGC AGC AAA TGT TGT AAA
THR PRO THR LEU VAL GLU VAL SER ARG ASN LEU GLY LYS VAL GLY SER LYS CYS CYS LYS 1445                      1460                          1475                        1490
CAT CCT GAA GCA AAA AGA ATG CCC TGT GCA GAA GAC TAT CTA TCC GTG GTC CTG AAC CAG
HIS PRO GLU ALA LYS ARG MET PRO CYS ALA GLU ASP TYR LEU SER VAL VAL LEU ASN GLN 1505                      1520                          1535                        1550
TTA TGT GTG TTG CAT GAG AAA ACG CCA GTA AGT GAC AGA GTC ACC AAA TGC TGC ACA GAA
LEU CYS VAL LEU HIS GLU LYS THR PRO VAL SER ASP ARG VAL THR LYS CYS CYS THR GLU
```

Fig. 5G

```
                           1565                        1580                         1595                         1610
TCC TTG GTG AAC AGG CGA CCA TGC TTT TCA GCT CTG GAA GTC GAT GAA ACA TAC GTT CCC
SER LEU VAL ASN ARG ARG PRO CYS PHE SER ALA LEU GLU VAL ASP GLU THR TYR VAL PRO 1625                        1640                         1655                         1670
AAA GAG TTT AAT GCT GAA ACA TTC ACC TTC CAT GCA GAT ATA TGC ACA CTT TCT GAG AAG
LYS GLU PHE ASN ALA GLU THR PHE THR PHE HIS ALA ASP ILE CYS THR LEU SER GLU LYS 1685                        1700                         1715                         1730
GAG AGA CAA ATC AAG AAA CAA ACT GCA CTT GTT GAG CTT GTG AAA CAC AAG CCC AAG GCA
GLU ARG GLN ILE LYS LYS GLN THR ALA LEU VAL GLU LEU VAL LYS HIS LYS PRO LYS ALA 1745                        1760                         1775                         1790
ACA AAA GAG CAA CTG AAA GCT GTT ATG GAT GAT TTC GCA GCT TTT GTA GAG AAG TGC TGC
THR LYS GLU GLN LEU LYS ALA VAL MET ASP ASP PHE ALA ALA PHE VAL GLU LYS CYS CYS
```

Fig. 5H

```
              1805                    1820                    1835                1850
AAG GCT GAC GAT AAG GAA ACC TGC TTT GCC GAC GAG GGT AAA AAA CTT GTT GCT GCA AGT
LYS ALA ASP ASP LYS GLU THR CYS PHE ALA ASP GLU GLY LYS LYS LEU VAL ALA ALA SER 1865                    1880                    1895
CAA GCT GCC TTA TAA GGC TTA TAA CAT CAC ATT TAA AAG CAT CTC AGC CTA CCA
GLN ALA ALA LEU  *  GLY LEU  *  HIS HIS ILE  *  LYS HIS LEU SER LEU PRO
              585 - STOP
```

Fig. 6

OLIGONUCLEOTIDE CODING FOR THE FIRST 6 CODONS OF THE cII GENE

```
          MetValArgAlaAsnLysArg
5'-AGCTTCATATGGTTCGTGCAAACAAACGCG-3'
    3'-AGTATACCAAGCACGTTTGTTTGCGCAGCT-5'
```

OLIGONUCLEOTIDE USED FOR THE DELETION MUTAGENESIS

```
5'-TCGTGCAAACAAACGCGCATGCACACAAGAGT-3'
   _____/_____/
          cII                SAH
```

SYNTHETIC NUCLEOTIDES USED IN
THE CONSTRUCTION OF cII-HSA

"PSEUDO-PRO-HSA" EXPRESSION PLASMID a to f: commercial HSA (sigma)

g to l: cII-HSA of microbiological origin ("pseudo-pro-HSA")

a, g: no trypsin b, h: 0.1 ug/ml trypsin c, i: 0.2 ug/ml trypsin d, j: 0.4 ug/ml trypsin e, k: 0.8 mg/ml trypsin f, l: 1.6 ug/ml trypsin

[HSA] 1 mg/ml, 1 hour's incubation at 37°C analysis nondenaturing 10% polyacrylamide gel Conversion of cII-HSA into mature HSA

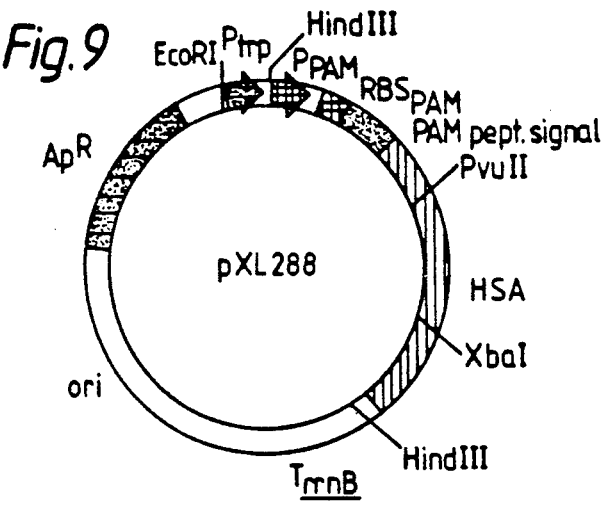

Fig. 9

Expression plasmid of the fusion "PAM-HSA signal peptide"

EcoRI
...GAATTCCCTGTTGACAATTAATCATCGAACTAGTTAACTAGTACGCAGCTTGGCTGCAGGT

Tryptophane promoter

Hind III
CGACCTGCAGCCAAGCTTCGTTGCTAGTATCAATTCGCTAATTATACACCTGCCAGAGGATACA

Promoter and fixation site of the PAM ribosomes

ATG AAA AAT AGA AAT CGT ATG ATC GTG AAC TGT GTT ACT GCT TCC CTG
Met Lys Asn Arg Asn Arg Met Ile Val Asn Cys Val Thr Ala Ser Leu

<<........PAM Signal sequence
                             ←——— sequence deleted for the construction of ATG TAT TAT TGG AGC TTA CCT GCA CTG GCT GAT GCA CAC AAG...
Met Tyr Tyr Trp Ser Leu Pro Ala Leu Ala Asp Ala His Lys...
..............................................>><<.....HSA .....
PAM1-HSA————————————————————————————>

Sequence of the expression signals and of the beginning of the
fusion "PAM-HSA signal peptide" of pXL288.

Fig. 10A

AMINO ACID SEQUENCES OF THE VARIOUS "PSEUDO-PRO" SEGMENTS

```
cII-HSA        MET VAL ARG ALA ASN LYS ARG-ASP
               ATG GTT CGT GCA AAC AAA CGC GAT..
                                              aa1 HSA

PAM1:          MET LYS ANS ARG ASN ARG-ASP
               ATG AAA AAT AGA AAT CGT GAT....

PAM2:          MET LYS ASN ARG LYS ARG-ASP
               ATG AAA AAT AGA AAA CGT GAT....

PAM3:          MET LYS LYS ARG LYS ARG-ASP
               ATG AAA AAA AGA AAA CGT GAT....
```

Fig. 10B

MODIFICATIONS PERFORMED ON PAM1

```
PAM3              LYS      LYS⟩
                   ↑        ↑ ⟩
PAM2                       LYS:
                   |        ↑
PAM1    MET LYS ASN ARG ASN ARG ASP
        ATG AAA AAT AGA AAT CGT GAT....
                   |        ↓
                   |        A⟩  modifications performed
                   ↓        ↓⟩  by oligonucleotide-
                   A        A⟩  directed mutagenesis
```

Fig. 11A

OLIGONUCLEOTIDE USED FOR THE DELETION MUTAGENESIS IN THE CONSTRUCTION OF PAM1-HSA (pXL641)

5'-ATGAAAAATAGAAATCGTGATGCACACAAGAGTG-3'
   _____/_____/
          PAM                HSA

Fig. 11B

OLIGONUCLEOTIDE USED FOR THE DIRECTED MUTAGENESIS IN THE CONSTRUCTION OF PAM2-HSA (pXL740)

5' CAATGAAAAATAGAAAACGTGATGCACACAAGAGT-3'
                     ↑
                     |
              modified nucleotide

Fig. 11C

OLIGONUCLEOTIDE USED FOR THE DIRECTED MUTAGENESIS IN THE CONSTRUCTION OF PAM3-HSA (pXL741)

5' AGGATACAATGAAAAAAAGAAAACGTGATGCACACAAGAGT-3'
                    ↑      ↑
                    |      |
              modified nucleotides

PROCESS FOR THE PREPARATION OF MATURE HUMAN SERUM ALBUMIN

This is a divisional of co-pending application Ser. No. 07/016,651 filed Feb. 19, 1987, now U.S. Pat. No. 5,100,784.

FIELD OF THE INVENTION

The present invention relates to the preparation of mature human serum albumin by a microbiological route.

BACKGROUND OF THE INVENTION

There is a wide choice of host organisms, such as modified mammal cells or microorganisms, which can potentially be used for the purpose of producing large quantities of human proteins of high therapeutic value.

The use of modified mammal cells with recombinant DNA techniques has the advantage of resulting in products which are closely related to those of natural origin; however, the culturing of these cells is intricate and can only be carried out on a limited scale.

The use of microorganisms such as bacteria permits manufacture on a larger scale, but introduces the disadvantage of producing products which differ appreciably from the products of natural origin. Thus, the proteins which are usually glycosylated in man are, in general, not glycosylated by bacteria [P. Berman and L. A. Laskey, Trends Biochem. Sci., (1985), 10, p.51 et seq]. Furthermore, human proteins which are expressed at a high level in bacteria such as *E. coli* frequently acquire an unnatural conformation which is accompanied by an intracellular precipitation [R. G. Schoner et coll., Bio. Technol. (1985), 3, p.151 et seq; J. M. Schoemaker et coll., EMBO J. (1985), 4, p.775 et seq]. Lastly, to enable a gene to be expressed in a bacterium, such as *E. coli*, it is essential that a methionine initiator codon is positioned before the coding sequence for the natural protein. In general, this residue is not excised by the methionyl aminopeptidase of *E. coli* [P. H. Seeburg et coll., 1985, 2, p.37 et seq; J. M. Schoner et coll., Proc. Natl. Acad. Sci. USA (1981), 81, p.5403].

The protein obtained thus has an abnormal amino acid as first residue, which can give rise to steric inhibition of biological activity when the beginning of the protein is involved in the activity. The residue may also be of an immunogenic character which is detrimental to the subsequent administration of the protein.

DESCRIPTION OF THE INVENTION

It follows that the choice of a host cell depends on the specific protein which it is intended to produce. In the case of a protein of high commercial value and required in limited quantity, mammalian cells may constitute a particularly highly suitable source. On the other hand, in the case of a product of lower commercial value and required in large quantity, of the order of several tens of tonnes, such as human serum albumin (HSA), it seems essential to employ microorganisms, while overcoming the disadvantages related to their use.

When the HSA is expressed from a genetic structure of the "Promoter-Beginning of translation site-ATG-Mature HSA gene" type, the protein produced generally retains methionine as an N-terminal residue. A number of methods may be envisaged in order to remove the N-terminal methionine from heterologous proteins expressed in *E. coli*, such as in vivo enzymatic cleavage, proteolytic excision during or immediately following the transport through the membrane, or in vivo proteolytic or chemical digestions.

It is known, in particular according to J. P. Waller, J. Mol. Biol., (1963), 1, p.483 et seq, that *E. coli* has a methionyl aminopeptidase which excises the N-terminal methionine in a number of proteins. However, the specificity of the mechanism is not well established and it is assumed that this mechanism depends on the residue or residues following the methionine [V.M. Vogt. J. Biol. Chem. (1970), 245, p.4760 et seq; H. J. George et coll., (1985) DNA, 4, p.273].

The secreted proteins are generally initially synthesized in the form of a preprotein comprising a "Signal-sequence" which includes the first residue. This sequence undergoes a proteolytic excision during or immediately following the transport through the membrane [R. Scheckman, Trends Biochem. (1985), 10, p.177]. However, this system is generally unsuitable in the case of cytoplasmic or heterologous proteins because of transport problems due either to some parts of the primary sequence of the protein [J. Tommassen et coll., EMBO J. (1985), 4, p.1041] or to an excessively fast intracytoplasmic precipitation of the protein. Furthermore, the mechanisms involved in the secretion of proteins by eukaryotic cells, such as the HSA secreted by hepatic cells, are probably quite different from the mechanisms of secretion involved in the case of microorganisms such as gramnegative bacteria [N. Wickner and H. Lodish, Science (1985), 230, p.400].

It has also been proposed to use chemical or enzymatic digestions in order to transform in vitro the protein which is synthesized by the bacterium in the form of a fused protein. The purpose of this transformation is the specific excision of a peptide sequence which is foreign to the desired protein, is situated in an N-terminal position, and which contains methionine as an initial residue. A simple example is that of a protein which does not naturally contain methionine residues [R. E. Chance et coll., "Peptides: Synthèses-Structure-Fonction", D. H. Rich and E. Gross, ed., Pierce Chem. Co, Rockford, Ill., (1981), p.721 et seq]. In this case, an in vitro treatment with cyanogen bromide enables the N-terminal methionine to be excised. However, this case is encountered only very rarely in the case of proteins of high molecular weight.

Some proteases, such as collagenase and the X factor, recognize a sequence of several amino acids, and this makes them relatively specific [K. Nagai and H. C. Thogerson, Nature (1984), 309, p.810 et seq; J. Germino and D. Bastia, Proc. Natl. Acad. Sci. USA (1984), 81, p.4692 et seq]. A genetic construction thus makes it possible to position the sequence which is recognized by the protease in question before the first amino acid of the required protein. This fused protein thus becomes a substrate for the protease, the main product of the reaction being the protein whose N-terminal position contains the same amino acid as the mature protein. However, the major disadvantage of this method lies in the price of the protease, especially when the problem is to produce a protein in large quantity.

Human cells synthesize HSA initially in the form of a prepro-HSA (FIG. 1). A signal sequence of 18 amino acids is removed when the HSA passes through the lumen of the endoplasmic reticulum and there still remain 6 amino acids at the N-terminal end (Arg- Gly-Val-Phe-Arg- Arg-) which are not present in the circulating HSA. According to S. O. Brennan and R. W.

Carrell, Biochim. Biophys. Acta (1980), 621, p.83 et seq, this propeptide does not appear to play any part in the secretion of HSA. It may be that a second specific proteolysis takes place in the Golgi apparatus or in the blood circulation system, the two arginine residues forming the site of recognition for a protease with a specificity which is similar to that of trypsin. In fact, an alternative form, known as "Christchurch albumin", which is due to a mutation which transforms the last arginine residue of the propeptide into glutamine, is not converted into mature albumin in vivo but is converted into Glu-HSA in vitro when the propeptide is treated with a low concentration of trypsin. Furthermore, mature HSA in natural form is resistant to trypsin under the same conditions [S. O. Brennan et coll., Biochim, biophys. Acta, (1984), 802, p.24 et seq].

The present invention provides a process for the preparation of a hybrid protein containing a hydrophilic N-terminal peptide elongation terminated by a preferential site for cutting with trypsin fused with the peptide sequence of mature human serum albumin, which comprises culturing a strain of *E. coli* capable of ensuring the maintenance of a plasmid containing a nucleotide sequence coding for the said N-terminal peptide extension fused to a nucleotide sequence coding for mature human serum albumin, the expression of said sequences being controlled by an inducible bacterial promoter. This hybrid protein may then be converted into mature human serum albumin by cutting with trypsin.

The process of the present invention may be operated by carrying out the following steps:

modifying in vitro the structural gene of HSA so that it has 6 additional codons coding for the first 6 amino acids of the cII protein of the lambda bacteriophage, and then linking the structural gene thus modified to the nucleotide sequence which naturally precedes the cII gene in the genome of the lambda bacteriophage and to a promoter which ensures a high level of transcription;

producing by means of a host bacterium containing the modified gene, a hybrid protein ("pseudo-pro-HSA") consisting of the first 6 amino acids of the cII gene followed by the mature HSA sequence;

denaturing, reducing and then renaturing the hybrid protein to produce a soluble protein whose conformation is similar to that of HSA of natural origin, and then modifying in vitro, using trypsin, the protein thus produced to excise the pseudo-pro-peptide and produce mature HSA.

It has also be found that mature HSA can be obtained by using an N-terminal peptide elongation ("pseudo-pro-peptide") in which the sequence differs from that of the first 6 amino acids of the cII protein of the lambda bacteriophage, provided that this extension permits an adequate expression of the fused protein, possesses the required hydrophilicity and comprises a site for cutting using trypsin. For example, the "pseudo-pro-peptide" may consist of the first 5 amino acids of the signal sequence of penicillin-amidase (6, if the first methionine residue is included).

BRIEF DESCRIPTION OF THE DRAWINGS

In the accompanying drawings:

FIG. 2 is a restriction map of the HSA gene showing three representative insertions;
FIG. 4 shows the complete nucleotide sequence coding for HSA in the plasmid pXL53;
FIG. 5 shows the protein sequence corresponding to the nucleotide sequence of FIG. 4;
FIG. 6 shows the structure of (A) an oligonucleotide coding for the first 6 codons of the cII gene and (B) an oligonucleotide used for deletion mutagenesis;
FIG. 9 shows the structure of the plasmid pXL288;
FIG. 10 shows amino-acid sequences for various pseudo-pro-HSA segments;
and
FIG. 11 shows three oligonucleotide sequences used for deletion mutagenesis in the construction of plasmids pXL641, pXL740, and pXL741.

Figure 1:
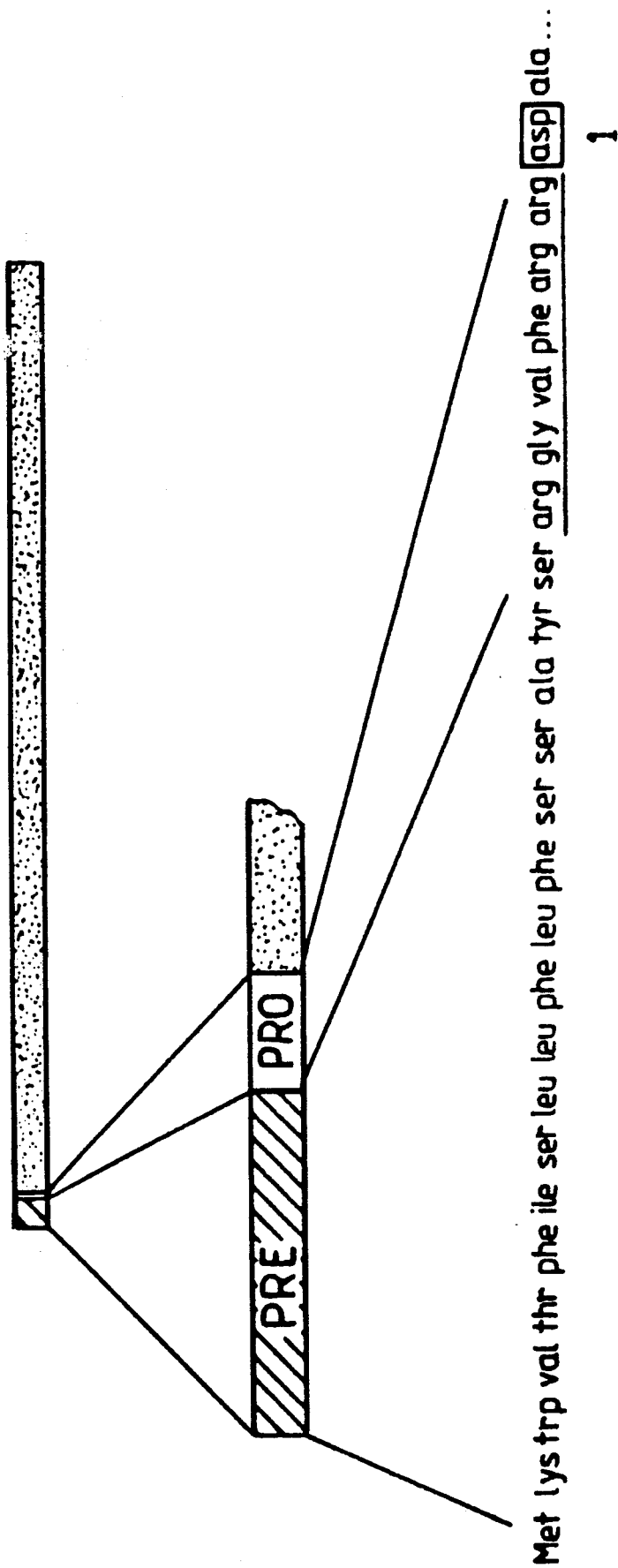
FIG. 1 shows the structure of prepro-HSA.
Figure 3A:
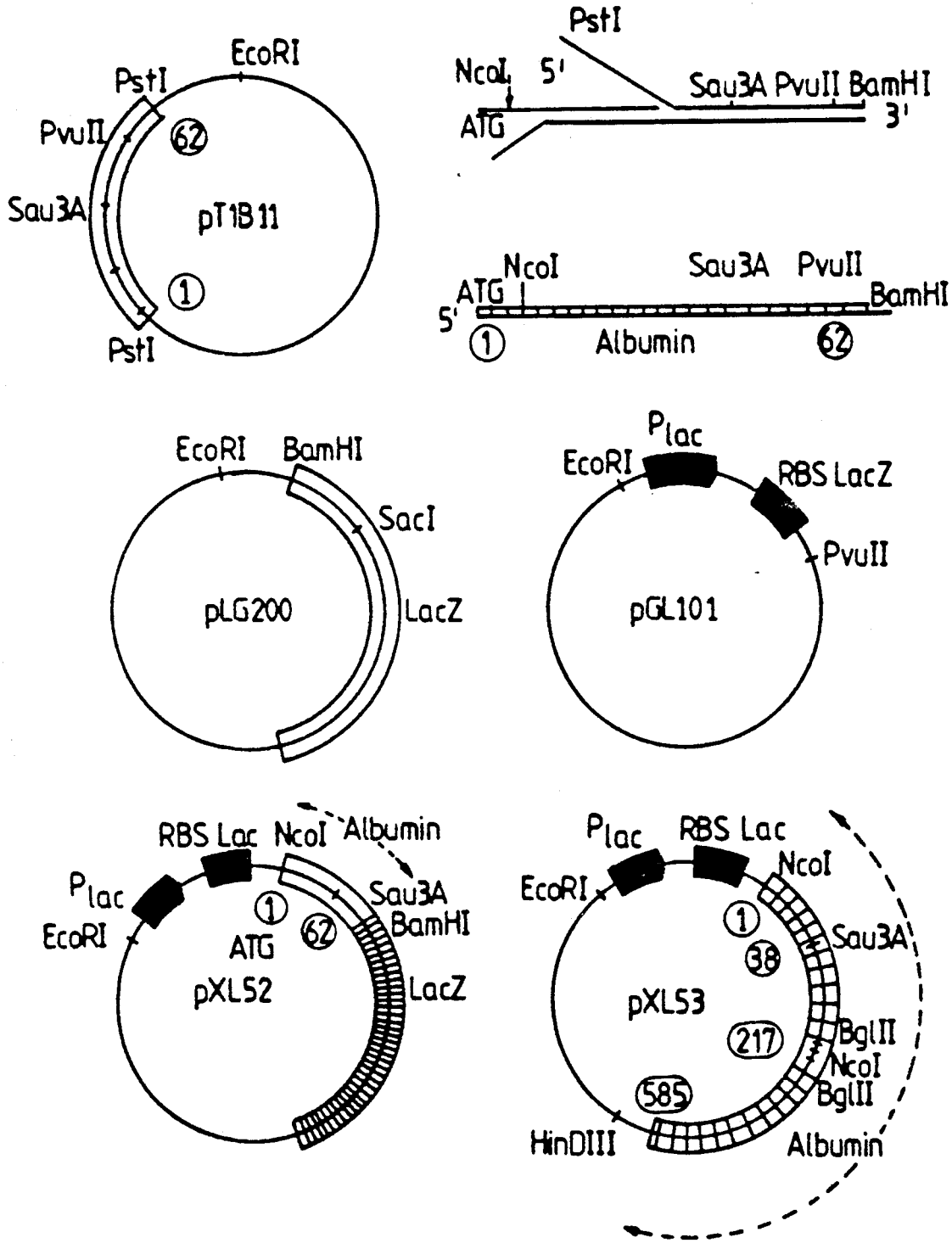
FIG. 3 illustrates the incorporation of the HSA gene into a plasmid.
Figure 3C:
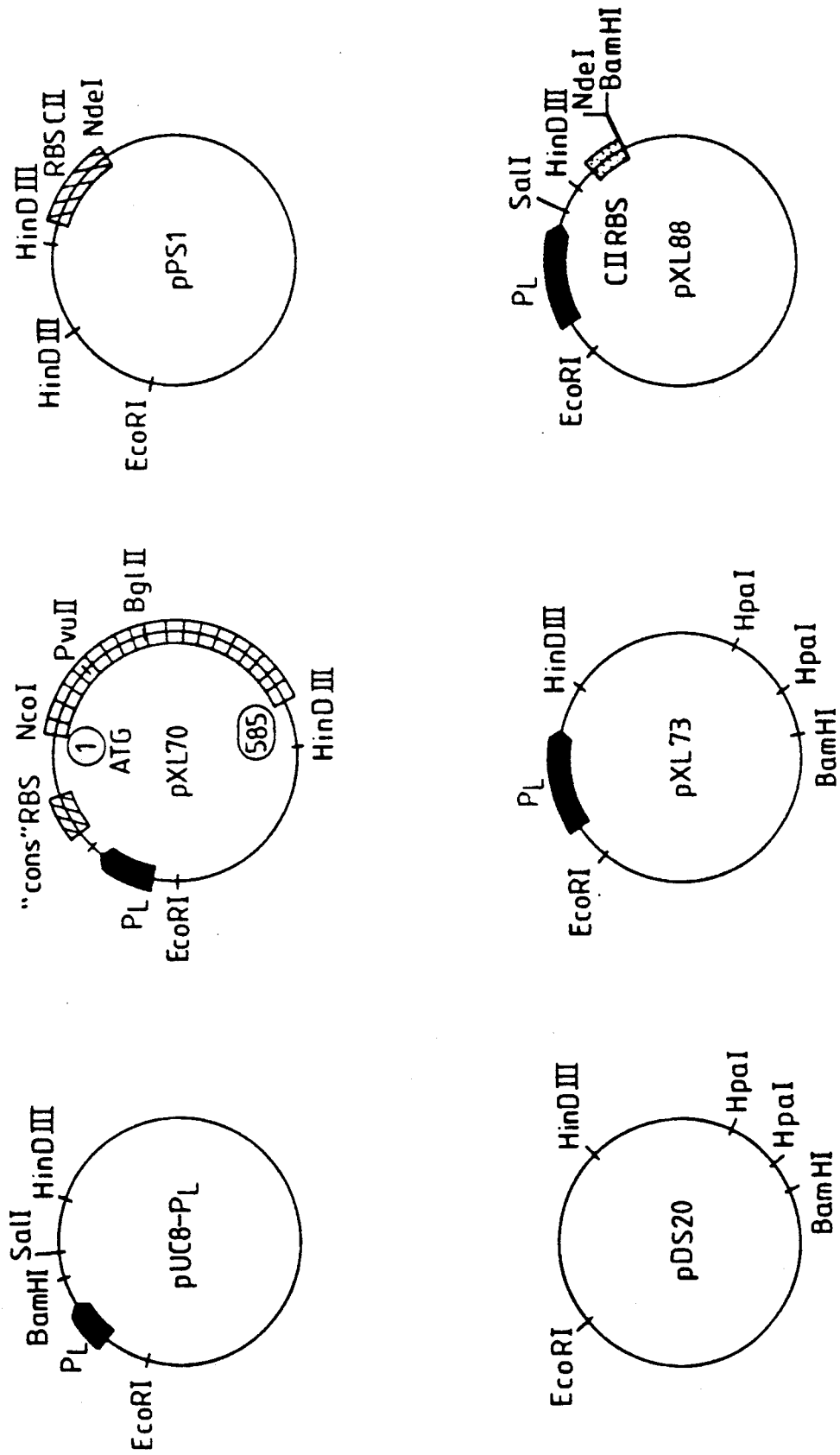
Figure 3D:
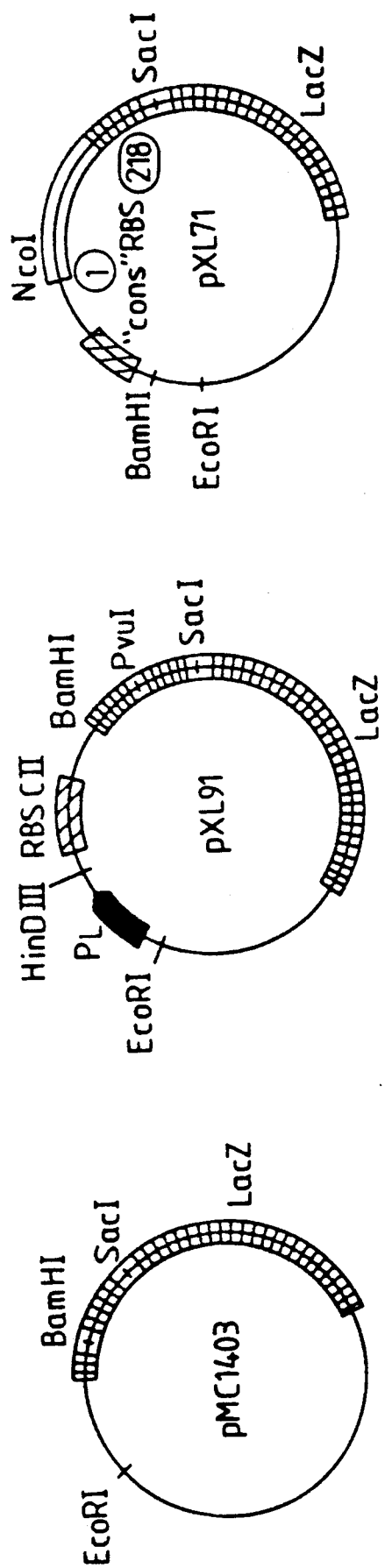
Figure 3E:
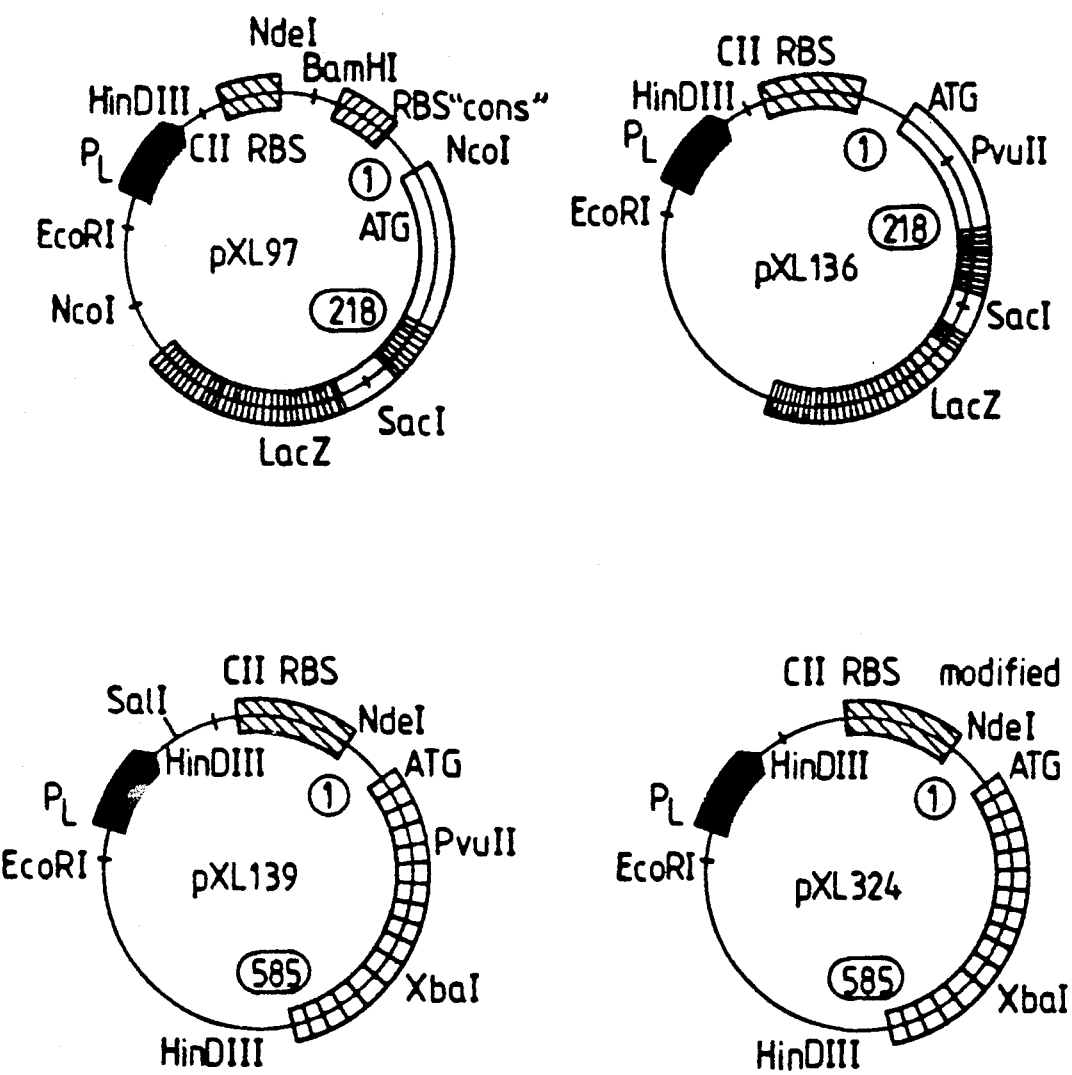

In the following text, the meaning of the technical terms employed in molecular biology is assumed to be known (cf., for example, J. Watson, "Biologie Molé culaire du Gène", French edition, Interéditions, 1978). The methods currently employed in molecular biology of the gene are described, for example, by T. Maniatis et coll., Molecular Cloning, Cold Spring Harbor Laboratory Press, New York, 1982. The construction, the gene expression processes, the renaturation and the conversion of the "pseudo-pro-HSA" by means of trypsin will be described in succession in the following text.

EXPERIMENTATION

A. CONSTRUCTION OF THE "pseudo-pro-HSA" GENE

1. Preparation of a Liver Messenger RNA

Human liver cells are obtained, for example, by biopsy, and the messenger RNA is extracted therefrom according to the method described, for example, by V. Glisin et coll., Biochemistry (1974), 13, p.2633 et seq; and by R. Deeley et coll., J. Biol. Chem. (1977), 252, p. 8310 et seq. The liver cells are treated with a 6M guanidine thiocyanate solution and the total RNA is purified using several precipitation cycles in ethanol at −20° C., centrifuging and redissolving the centrifuged pellet.

The messenger RNA preparation is enriched using several cycles of affinity chromatography on columns of oligo (dT)-cellulose, according to the technique described by H. Aviv and P. Leder, Proc. Natl. Acad. Sci. (USA) (1972), 69, p.1408 et seq. The messenger RNA isolated in this manner, containing 1 to 2% of total RNA, is stored in aqueous solution at −70° C.

The proportion of messenger RNA specific human serum albumin within the total population can be determined (for example by in vitro translation of an aliquot of the RNA solution in rabbit reticulocyte lysates). One method consists in using the lysate of reticulocytes supplied by the Amersham company, according to the protocol recommended by this supplier. It is thus possible to determine the fraction of newly formed protein which is capable of being immunoprecipitated by antialbumin antibodies within all the newly formed proteins. For example, a fraction of the order of 6% is obtained.

2. Synthesis of cDNA and Cloning in *E. coli* a. Synthesis of the first strand

Using the technique according to G. N. Buell et coll., J. Biol. Chem. (1978), 253, p. 2471 et seq, modified, for example 5 μg of total messenger RNA is used in a final volume of 50 microliters of a solution containinning: 100 mM of Tris-HCl of pH 8.3, 10 mM of MgCl$_2$, 0.4 mM of DTT, 20 mM of KCl, 0.4 mM of Na pyrophosphate, 1 mM of each nucleotide triphosphate (dNTP), 100 µg/ml of oligo (dT)$_{12-18}$, 0.5 U/ml of ribonuclease inhibitor, 50 picomoles of radio active tracer and 40 units of reverse Transcriptase (Life Science Company Inc.).

The reaction of reverse transcription of the messenger RNA into complementary DNA (cDNA) is continued for 1 hour at 42° C.

The proportion of cDNA synthesis is calculated by measuring the degree of incorporation of the radioactive tracer into acid-precipitable molecules, using a known technique.

After 1 hour, the reaction is stopped by the addition of EDTA (20 mM), and the messenger RNA is destroyed by alkaline digestion in 50 mM of NaOH, for 3 hours at 42° C.

The newly formed cDNA is separated from the unincorporated dNTPs and from the products of alkaline degradation of the RNAs using chromatography, for example, on a column of Sephadex G100 (trademark of Pharmacia Fine Chemicals). 1.5 µg of single-strand cDNA are produced from 5 µg of total messenger RNA.

b. Synthesis of the second strand

The single-strand cDNA is converted into twin-strand DNA using the action of the "Klenow" fragment of DNA polymerase I.

The reaction conditions are: 100 mM of Hepes of pH 7, 10 mM of MgCl$_2$, 2.5 mM of DTT, 70 mM of KCl, 0.5 mM of each dNTP, and 50 units of the "Klenow" fragment of DNA polymerase I (marketed, for example, by the company New England Biolabs Inc.).

The reaction is continued for 15 hours at 15° C. and the twin-strand DNA is separated from the unincorporated dNTPs again, using chromatography on a column of Sephadex (trademark) G100.

c. Cloning of the twin-strand DNA

To eliminate the molecules of single-strand DNA and to produce a twin-strand DNA with flush ends, the unpaired sequences are treated with nuclease S$_1$ according to the technique described by A. Efstradiatis et coll., Cell (1976), 7, p. 279 et seq. The newly formed twin-strand DNAs are separated according to their size by centrifuging in a sucrose gradient. In general, use is made of a 5% -20% gradient of sucrose in 50 mM of Tris-HCl of pH 8.5, 10 mM of EDTA, 800 mM of NaCl, centrifuged at 210,000 g for 15 hours at 20° C., and a fractionation of the gradient into aliquots is performed after centrifuging.

The size of the molecules in each fraction is monitored by electrophoresis of specimens carried out in parallel with standards of DNA of known sizes, and the fractions containing a DNA consisting of the concatenation of more than 500 base pairs are collected together.

To permit the cloning of this DNA, its 3' ends are first elongated using oligo(dC), and the 3' ends of the PstI site of the pBR322 vector plasmid are elongated in parallel using oligo(dG) in accordance with the technique of F. Rougeon et coll., J. Biol. Chem. (1977), 252, p.2209 et seq.

The twin-strand DNA described above is then hybridized with the vector plasmid, using, for example, the technique of L. Villa Komaroff et coll., Proc. Natl. Acad. Sci. (USA) (1978), 75, p. 3727 et seq.

A "bank" of liver cDNA clones is created by transforming the bacterium *E. coli* with the DNA thus described using the method described by M. Mandel and A. Higa, J. Mol. Biol. (1970), 53, p.154 et seq. and M. Dagert and S. D. Erlich, Gene (1979), 6, p. 23 et seq.

d. Location of the albumin cDNA clones

A colony hybridization technique is used with the aid of synthetic oligonucleotides, the sequences of which are deduced from the protein sequence of human albumin (B. Meloun et coll., FEBS Letters (1975), 58, p. 134 et seq; M. Grunstein and D. Hogness, Proc. Natl. Acad. Sci. (USA) (1975), 72, p. 3961 et seq; R. B. Wallace et coll., Nucleic Acids Res. (1981), 9, p. 879, et seq.). After growth at 37° C. followed by amplification in the presence of 250 ug/ml of chloramphenicol, the bacterial in the colonies obtained are lysed with sodium hydroxide and the denatured DNA from lysed cells is hybridized with 5' labelled oligonucleotides in a solution containing: 5×SSC, 0.5% NP 40, 100 µg/ml of salmon sperm DNA denatured by boiling and cooled rapidly in ice, and 0.5 ng/ml of the labeled oligonucleotide. The hybridization is performed at 37° C. for 18 hours. The filters are then washed in 5×SSC, at 25° C., then at 37° C., then at 45° C. and this is done four times, 15 minutes at each stage.

The filters are then exposed on Kodak (trademark) X-OMAT films at −70° C., with an intensifying screen, for 15 to 24 hours. The clones forming hybrids with the probes are isolated again and then lysed. The plasmid DNA is purified by centrifuging in a caesium chloride-ethidium bromide medium using a known technique.

The insertion DNA is sequenced using the technique of Maxam-Gilbert (A. Maxam and W. Gilbert, Methods Enzymol. (1980), 65, p. 499 et seq) to compare the proteinic sequence derived from the nucleotide sequence with that of the human serum albumin.

In this way, a series of clones is identified in which the insertions correspond to the whole of the human serum albumin gene.

FIG. 2 shows the restriction map of the serum albumin gene, together with the position of three of the most representative insertions, denoted by "pT1B11", "pAA38", and "p6D8".

e. Incorporation of an initiation codon in the structural gene (FIG. 3)

a) The DNA of the plasmid "pT1B11" is digested with PstI and PvuII enzymes, and a DNA fragment containing 125 base pairs, corresponding to the sequence of the 5' end of the serum albumin gene including the nucleotides coding for (amino acids nos. 1 to 62) is isolated. A DNA linker fragment [d(CCGGATCCGG)] corresponding to the BamHI enzyme recognition site is ligated to the PvuII DNA end to generate a PstI-BamHI fragment.

Separately, there is prepared a synthetic oligonucleotide, 21 bases in length, which has an "ATG" triplet before the nucleotides coding for the amino acids of human serum albumin, as well as an NcoI restriction site, and whose sequence is the following: 5'GAATC-CATGGATGCACACAAG 3'.

The PstI-BamHI DNA fragment is denatured and is hybridized with the synthetic oligonucleotide. The hybridization is performed using the sequence 5' . . . GATGCACACAAG 3', the 3' end of the complementary DNA strand being unpaired. The unpaired ends are digested and then polymerization is carried out in the direction 5' . . . 3' with the "Klenow" fragment of DNA polymerase I, in accordance with the techniques of H.

Jacobsen et coll., Eur. J. Biochem. (1974), 45, p. 623 et seq.

This produces a fragment containing a flush end at 5', an NcoI site and then the ATG triplet and a BamHI site at 3'.

b) The ligation of three DNA fragments is performed:

1) an EcoRI-BamHI fragment of the "pLG200" plasmid (L. Guarente et coll., Cell (1980), 20, p. 543 et seq) bearing an antibiotics resistance gene, the replication origin and the 3' end of the β-galactosidase gene,
2) an EcoRI-PvuII fragment of the "pGL101" plasmid (G. Lauer et coll., J. Mol. Appl. Genet. (1981), 1, p. 139 et seq) bearing the $P_{lac}$ promoter and the fixation site of a ribosome (RBS) of the lacZ gene of E. coli,
3) the mutagenized DNA fragment coding for the first 62 amino acids of human albumin.

A plasmid (pXL52) is isolated, which plasmid produces a fusion of the 5' end of the human serum albumin gene with the β-galactosidase gene of E. coli.

f) Construction of the complete gene (FIG. 3)

The DNA of the plasmid "p6D8" is digested with EcoRI, and partially with BgLII, using a technique which has already been described. The large fragment EcoRI-BgLII is isolated; it contains the sequence coding for the last 405 amino acids of human serum albumin and then the replication origin of the plasmid and the tetracycline resistance gene.

The DNA of the plasmid "pXL52" described above is digested with EcoRI and Sau3A, and a fragment containing 200 base pairs is isolated.

The DNA of the plasmid "pAA38" is digested with Sau3A and a fragment containing 540 base pairs is isolated.

The three fragments are spliced (in the order [pXL52-EcoRI-Sau3A]-[pAA38-Sau3A]-[p6D8 Bg(II-EcoRI]), making use of the compatibility between the sites Sau3A and BgLII. A plasmid called "pXL53" is produced, whose structural quality is controlled by a complete sequencing of the fragment included between the site EcoRI and the site PstI corresponding to the junction between the insertion and the vector plasmid.

The complete nucleotide sequence, together with the derived protein sequence, are shown in FIGS. 4 and 5.

The changes observed between this sequence and the published protein sequence (B. Meloun et coll., FEBS Letters (1975), 58, p. 134 et seq; M. Dayhoff, Atlas of Protein sequence and structure (1978), 5, supplement 3, p. 306) are the following:

| Position | Meloun et coll. | Human serum albumin deduced from the sequence of "oXL53" |
|---|---|---|
| 131 | Glutamine | Glutamic acid |
| 364 | Histidine | Alanine |
| 367 | Tyrosine | Histidine |
| 370 | Alanine | Tyrosine |
| 381 | Valine | Methionine |
| 464 | Glutamic acid | Histidine |
| 465 | Histidine | Glutamic acid |
| 501 | Glutamine | Glutamic acid |

3. Construction of Expression Systems for Human Methionylserum Albumin a. Use of the lambda bacteriograph promoter "$P_L$"

The plasmid "pXL53" is linearized by partial digestion with the enzyme NcoI, only the NcoI site in the 5' position of the initiation codon being taken into consideration, and flush edges are formed by filling according to the technique of R. M. Wartell and W. S. Reznikoff, Gene (1980), 9, p. 307 et seq).

An "adaptor" is synthesized, which contains in the 5' position a sequence corresponding to the recognition site for a restriction enzyme such as BamHI, and then a sequence corresponding to a ribosome binding site ("consensus" or "theoretical" RBS). The adaptor sequence is: 5'GGATCCTAGGAGGAAC 3'.

The ligation of the adaptor in the 5' position of a DNA containing flush edges has been described, for example, by C. P. Bahl et coll., Gene (1976), 1, p. 81 et seq.

The method consists in performing the reaction on 20 microlIters of a solution containing 50 mM of Tris-HCl of pH 7.5, 10 mM of $MgCl_2$, 15 mM of DTT, 1 mM of ATP, 50 μg/ml of adaptor, 20 μg/ml of DNA and 1 unit of DNA-ligase (New England Biolabs Inc.). The reaction is continued for 10 hours at 15° C. This ligation creates a BamHI site without deleting the NcoI site.

The ligation product is digested with BamHI and with HinDIII. Because of the presence of an HinDIII site in the 3' position of the human serum albumin gene, a DNA fragment containing the entire coding sequence is produced.

The HinDIII-BamHI fragment thus produced is subcloned, for example in the "pBR322" plasmid by transforming E. coli according to the method already described above, to produce the plasmid "pXL61".

The pXL61" plasmid contains no promoter.

The lambda bacteriophage promoter "$P_L$" is placed on the bacteriophage chromosome between a BglII site and a BamHI site (see E. Szybalski and W. Szybalski, Gene (1979), 7, p. 217 et seq), and whose nucleotide sequence is known (F. Sanger et coll., J. Mol. Biol. (1982), 162, p. 279 et seq). This fragment may be cloned and its restriction sites may be modified using known methods.

It is noted that the plasmids bearing $P_L$ need to be propagated in strains of E. coli bearing the repressor gene cI, this being done so that this promoter is not expressed in a constitutive manner.

In a first construction, $P_L$ is available in the form of a fragment BamHI from the plasmid "pPL-lambda" (Pharmacia P.L. Biochemicals). The insertion of this BamHI fragment into the BamHI site of the plasmid "pXL61" makes it possible to produce the plasmid "pXL65", in which it has been confirmed that the orientation of the promoter in relation to the structural gene for human serum albumin is correct.

Other constructions may be produced from available plasmids. It is possible, for example, to excise from the plasmid "$pP_L$-lambda" an HaeIII-HaeIII fragment containing the promoter $P_L$ and to insert it into the SmaI site of a multisite cloning sequence carried on a plasmid, such as the plasmid "pUC8" (J. Veira and J. Messing, Gene, (1982), 79, p. 259 et seq) to produce "pUC8-$P_L$"" in which the EcoRI site is in the 5' position of the promoter.

Starting with the "pPS1" plasmid (P. Sarmientos et coll., Cell (1983), 32, p. 1337 et seq), it is possible first of all to destroy the HinDIII site closest to the NdeI site (FIG. 3) and then to replace the small EcoRI-HinDIII fragment with, on the one hand, the EcoRI-BamHI fragment of the "pUC8-$P_L$" plasmid containing the promoter $P_L$ and, on the other hand, the BamHI-Hin- DIII fragment of the "pXL61" plasmid containing the serum albumin gene. This produces the "pXL70" plasmid in which the assembly: "$P_L$-"Consensus"RBS-ATG-human serum albumin gene" is carried on an EcoRI-HinDIII DNA fragment.

b. Replacement of the "consensus" RBS with that of the cII gene of the lambda bacteriophage The cII gene of the lambda bacteriophage, whose sequence and initiation site are known, may be translated with effectiveness (E. Schwarz et coll., Nature (1978), 272, p. 410 et seq.).

A plasmid containing the expression system ""$P_L$" promoter - cII RBS - ATG - serum albumin gene" is constructed.

For example, after the BamHI site of "pUC8-$P_L$" has been destroyed by the action of the enzyme S1 (A. J. Berk and P. A. Sharp, Cell (1977), 12, p. 72) it is possible to isolate an EcoRI-HinDIII fragment containing the $P_L$ promoter and then to ligate this fragment to the large EcoRI-HinDIII fragment of the "pDS20" plasmid (G. Duester et coll., Cell (1982), 30, p. 855 et seq), to produce the plasmid "pXL73".

The RBS of the cII gene is extracted from the plasmid "pPS1". This plasmid is digested with NdeI and a BamHI adaptor is inserted after forming flush ends. The RBS is then excised in the form of an HinDIII-BamHI fragment.

A "pXL88" plasmid is constructed first of all, in which this HinDIII-BamHI fragment is ligated to the large HinDIII-BamHI fragment of the plasmid "pXL73". In the new plasmid "pXL88", the cII RBS is inserted with the appropriate orientation in relation to the $P_L$ promoter, the whole in a multisite system so that the $P_L$-cII RBS assembly is carried on an EcoRI-BamHI DNA fragment consisting of 578 base pairs.

The 578 base pair EcoRI-BamHI fragment is subcloned between the EcoRI and BamHI sites of the plasmid "pMC1403" (M. J. Casadaban et coll., J. Bacteriol. (1980), 143, p. 971 et seq) which carries the β-galactosidase gene (lacZ) after the BamHI site. This construction leads to the plasmid "pXL91" in which the β-galactosidase gene is expressed under control of the system "$P_L$-cII RBS".

The BamHI-BglII fragment of the "pXL61" plasmid described previously is subcloned in the BamHI site of the plasmid "pMC1403". (The ligation of a BglII site in a BamHI site is possible, but the excision by BamHI at BglII is not possible any more; only one BamHI site therefore remains).

This construction ("pXL71") leads to the insertion of a 700 base pair DNA fragment comprising the sequence "BamHI-["consensus" RBS]-ATG-NcoI-partial gene of the serum albumin (coding for the amino acids 1 to 218)-β-galacosidase gene".

This plasmid is cut using BamHI and SacI (the SacI site is present in the β-galactosidase gene) and is inserted into the "pXL91" plasmid described previously in the place of the pre-existing BamHI-SacI fragment.

The product is then the "pXL97" plasmid whose insertion has the following structure: "EcoRI site-$P_L$-cII RBS-BamHI site-"consensus" RBS-NcoI site-ATG -partial gene of the serum albumin-β-galactosidase gene".

The "pXL97" plasmid is digested with BamHI and partially with NcoI, consideration being given only to the NcoI site close to the initiation codon, and the flush edges are formed by the action of the nuclease S1, and it is then again closed onto itself. This manipulation, on the one hand, eliminates the "consensus" RBS DNA sequence and, on the other hand, puts an ATG of the cII RBS in phase with the serum albumin sequence.

This produces the plasmid "pXL136" which comprises the sequence "EcoRI site-$P_L$-cII RBS-ATG-partial gene of the serum albumin-β-galactosidase gene".

Since the partial gene of the serum albumin has a PvuII site, the plasmid "pXL136" is digested with EcoRI and PvuII and a 760 base pair fragment is extracted, and this is inserted between the EcoRI and PvuII sites of the plasmid "pXL70", described previously. This produces the plasmid "pXL139" which carries the structure "$P_L$-cII RBS-complete serum albumin gene" on an EcoRI-HinDIII fragment, like the plasmid "pXL70", and which carries the "consensus" RBS substitution by that of the cII gene.

The plasmid "pXL139" described previously is sectioned at the only SalI site, between the $P_L$ promoter and the cII RBS. The DNA is digested with the enzyme Bal31, so that the tR1 transcription end site in the 5' position of the cII RBS is digested and then an HinDIII adaptor is added and the HinDIII-XbaI fragment containing the cII RBS amputated from tR1 and the first 357 codons of the human serum albumin gene is isolated. This HinDIII-XbaI fragment is combined with, on the one hand, the XbaI-EcoR1 fragment of the pXL139 plasmid containing the end of the human serum albumin gene and, on the other hand, the EcoR1-HinDIII fragment bearing the $P_L$ promoter obtained from the pUC8-$P_L$ plasmid after destruction of the BamHI site. The plasmid pXL324 is produced in this manner.

4. Construction of an Expression Plasmid for the "Pseudo-pro-HSA"

A DNA fragment is constructed by hybridization of two synthetic oligonucleotides having the structure given in FIG. 6A. The sequence contains an "ATG" starting codon followed by the first 6 codons of the lambda bacteriophage cII gene. This fragment has one cohesive end of HinDIII type and another cohesive end of SalI type. This synthetic fragment is cloned between the HinDIII and SalI sites of the M13mp10 vector (J. Messing, Methods Enzymol., (1984), 101, p. 20 et seq). The DNA in a replicative form, purified from infected cells by means of the resultant bacteriophage, is used in the next stage of construction.

A 765 base pair SalI-BglII fragment originating from the pXL324 plasmid containing the beginning of the gene (cDNA) coding for the HSA is cloned in this recombining bacteriophage. The E. coli strain JM101 is infected by means of this new bacteriophage and the supernatant of a 5-hour culture is used as source of phage particles containing the single-strand DNA characteristic of the filamentous phages of M13 type. This single strand is then used as a matrix for an oligonucleotide directed mutagenesis which makes it possible to eliminate the sequence included between the sixth codon of the cII gene and the first codon of the mature HSA (GAT) according to the methods described, for example, by J. P. Adelman et coll., DNA (1983), 2, p. 183. The oligonucleotide employed in this directed mutagenesis is described in FIG. 6B. The resultant phage contains the beginning of a new fused gene. The structure of the DNA fragment employed in the subsequent constructions is verified using the enzyme sequencing method (F. Sanger et coll., Proc. Natl. Acad. Sci. USA, (1977), 74, p. 5463).

Figure 7:
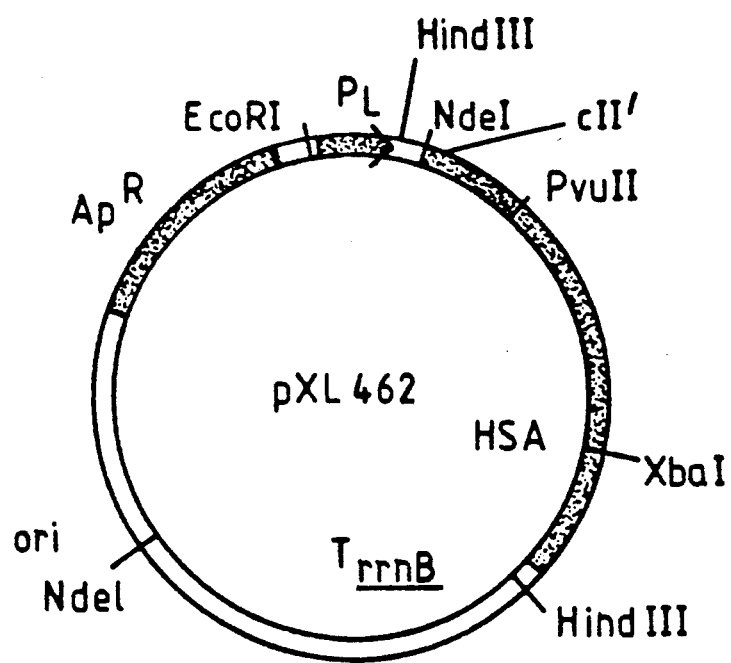
FIG. 7 shows the structure of the plasmid pXL462.

A reconstruction of the complete gene coding for the "pseudo-pro-HSA" fusion is then performed. A vector containing an ampicillin resistance gene, a replication origin, a transcription terminator and a part of the cDNA coding for the HSA is prepared from the plasmid pXL70 by treating this plasmid with the restriction enzymes EcoRI and PvuII. The fragment containing approximately 7200 base pairs is purified by agarose gel electrophoresis and electroelution. A 430 base pair fragment containing the $P_L$ promoter and the modified cII gene binding site (RBS) is purified from a digestion of the plasmid "pXL324" by the EcoRI and NdeI enzymes using polyacrylamide gel electrophoresis and electroelution. A 200 base pair NdeI-PvuII fragment containing the beginning of the cII-HSA hybrid gene is purified from the replicative form of the recombined M13 bacteriophage modified by in vitro mutagenesis described above. A ligation reaction involving three partners has been performed. The resultant plasmid is called "pXL462" (FIG. 7).

The plasmid "pXL462" has been introduced into the strain G819 using transformation. This strain is derived from the strain E103S (L. SIMON, Waksman Institute for Microbiology, Rutgers-The State University, Piscataway, N.J.,USA) by transformation with the plasmid pRK248cLts (H-U. Bernard et coll., Gene (1979), p. 59 et seq). This plasmid is compatible with "pXL462" and carries the Lambda bacteriophage cI gene which codes for a heat-sensitive repressor of the $P_L$ promoter. In fact, this repressor becomes inactive above 38.5° C. The strain produced bears the number G1398.

Starting with the plasmid pXL462, other plasmids have been constructed where the $P_L$ promoter included on an EcoRI-HinDIII restriction fragment has been replaced with various inducible bacterial promoters. The construction of these plasmids has employed the single XbaI site of pXL462 and a three-partner ligation reaction of the type of that described above (see FIG. 7). Since the present invention does not depend on the type of bacterial promoter used, only the case of the plasmid pXL462 carrying the $P_L$ promoter will be referred to in the following text.

B. PRODUCTION OF cII-HSA BY A MICROBIOLOGICAL ROUTE

1. Culture and Induction

Starting with a reisolation of the G1398 strain in a Petri dish with agar gel based on an LB medium containing 50 micrograms/ml of ampicillin (pLBA), incubated beforehand at 30° C., a preculture is diluted 100 fold in the same medium and the culture is incubated at 30° C. with agitation. When the optical density read off at 610 nanometers reaches 1.0, the culture is then heated to 42° C. for 90 minutes, with agitation.

2. Sonication, recovery of the cII-HSA

The cell pellet collected after centrifuging is resuspended in PBS (0.2 g/l of KCl, 0.2 g/l of $KH_2PO_4$, 8 g/l of NaCl and 1.25 g/l of $Na_2HPO_4$ in a volume corresponding to 1/30th of the initial volume of the culture. After incubation for 15 minutes at a temperature in the region of 20° C. in the presence of egg-white lysozyme at a concentration of 1 mg/ml, sonication of the bacteria is performed at 0° C., for example, using a Branson (model B30) sonicator in continuous mode for two periods of six minutes with cooling. The insoluble fraction is collected by centrifuging at 12,000 g at 4° C. for 15 minutes and is then washed with PBS and dried under vacuum at 30° C. for 15 minutes.

3. Denaturation, Reduction and Renaturation

The sonification pellet containing the insoluble products originating from 1 liter of culture is taken up in 4 ml of denaturing and reducing solution (6M of guanidine-HCl, 0.1M of $KH_2PO_4$ at pH 7.5, 0.1M of $\beta$-mercaptoethanol). The suspension produced in this manner is shaken gently in a closed tube for 16 hours at 4° C. A virtually clear solution is then obtained. A slight insoluble precipitate is removed by centrifuging. A 1/100 dilution of the supernatant is performed in a renaturing solution (50 mM of Tris-HCL at pH 8.5, 100 mM of NaCl, 1 mM of EDTA) and this mixture is left for 24 hours at 4° C. The solution is then centrifuged to remove a whitish opalescence. The supernatant produced is concentrated approximately 100 times by ultrafiltration (membrane with a "cut-off" of 30,000 daltons; for example, by using the Millipore CS-30 single-use ultrafiltration units), and is clarified again by centrifuging and is then dialysed against a pH 7.5, 20 mM phosphate (Na) buffer. The cII-HSA fusion protein (pseudo-pro-HSA) produced in this manner is more than 90% homogeneous according to an analysis by electrophoresis on SDS polyacrylamide gel.

4. Conversion of the cII-HSA into Mature HSA

A solution of trypsin (prepared, for example, from freeze-dried trypsin for analytical use, marketed by Boehringer Mannheim) is prepared in the reaction solution. The cII-HSA is treated at a concentration, for example, of the order of 1 mg/ml with a quantity of trypsin of between 1/5,000 and 1/1,000 (in relation to the mass of the HSA) for 30 to 60 minutes at 37° C. in a pH 7.5, 50 mM phosphate (Na) buffer, with 50 $\mu$M $CaCl_2$.

5. Verification of the Interruption

Figure 8:
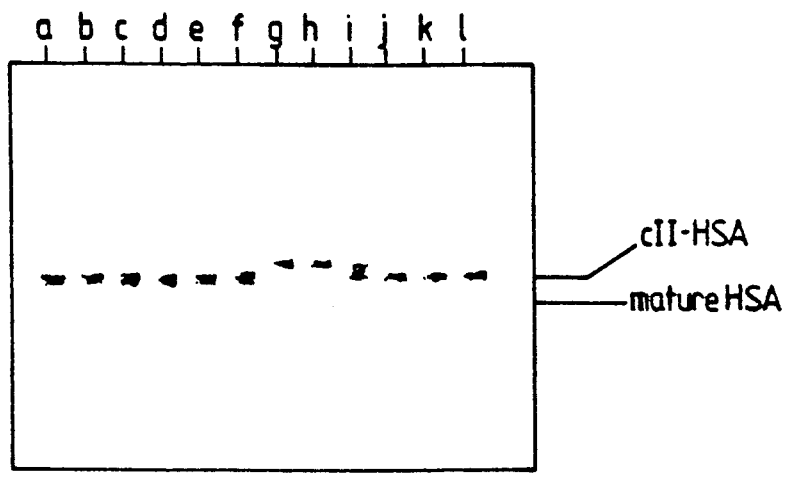
FIG. 8 is a diagram of an electrophoresis pattern illustrating the conversion of cII-HSA into mature HSA.

The conversion reaction can be followed using trypsin on a nondenaturing polyacrylamide gel (FIG. 8). Because of the presence of several positively charged amino acids in the N-terminal hexapeptide, the electrophoretic migration of the cII-HSA is slower on a gel of this type than that of the natural HSA. FIG. 8 shows that commercial HSA is not significantly modified by trypsin within the concentration range employed. On the other hand, cII-HSA is converted by the action of trypsin into a molecule which migrates together with commercial HSA. The N-terminal sequence of this trypsin-modified protein has been examined by Edman degradation and the results obtained do confirm that the proteolysis site is situated after the Lys-Arg dipeptide, at the end of the cII portion of the hybrid protein. On a basis of the reported amino acid sequence of natural HSA (Meloun, loc cit), the recombinant human serum albumin obtained in this way also contains aspartic acid as an N-terminal residue and only differs from authentic human serum albumin by the variations mentioned.

The construction of the plasmid "pXL288" has been described in European Patent Application EP 86/400,618.4, published under the number 200,590, in the name of the applicant company. After being introduced into an appropriate strain of E. coli, this plasmid (FIG. 9) permits the high level expression of a hybrid protein, not matured in vivo, consisting of the fusion between the signal peptide of the penicillin G amidase (PAM) (EC 3.5.1.11; penicillin aminohydrolase) of *E. coli* and mature HSA.

The plasmid "pXL288" is characterized in that it contains the Ptrp promoter of the tryptophane operon of *E. coli* upstream of the PAM promoter, the ribosome binding site of the PAM gene, the ATG initiation codon and the nucleotides of the PAM signal peptide, which are fused with the structural gene for HSA.

The N-terminal end of the leader peptide of the PAM contains a sequence of 5 basic amino acids. This basicity forms one of the general characteristics of a secretion signal peptide (M.E.E. Watson, Nucl. Acids Res., 12, p. 5145 et seq). It has now been found that the first 6 amino acids of this signal peptide (Met Lys Asn Arg Asn Arg-, "PAM 1") can act as a "pseudo-pro" sequence.

To this end, the nucleotides corresponding to the amino acids 7 to 26 of the leader peptide of the PAM have been eliminated in order to fuse precisely the "PAM1" sequence to the sequence of mature HSA using the oligonucleotide-directed suppression technique described previously (FIG. 9). The oligonucleotide which enables this suppression to be performed is shown in FIG. 11A. The modified sequence is then substituted in the plasmid "pXL288" to give the plasmid "pXL641" whose structure is as follows: "EcoR1-Ptrp-Sal1-[PAM promoter-PAM RBS-nucleotide sequence coding for PAM1]-HSA gene".

Two derivatives of the sequence "PAM1" are constructed by oligonucleotide-directed mutagenesis, after subcloning in the bacteriophage M13mp18amIV, according to the method described by P. Carter et coll., Nucl. Acids Res., 1985, 13, p. 4431 et seq. The oligonucleotides enabling this mutagenesis to be performed are shown in FIGS. 11B and 11C. After reconstruction, two plasmids similar to the plasmid "pXL641" containing the sequences coding for "PAM2" (Met Lys Asn Arg Lys Arg-; plasmid "pXL740") and "PAM3" (Met Lys Lys Arg Lys Arg-; plasmid "pXL741") are obtained (FIG. 10).

After the introduction of the plasmids "pXL641", "pXL740" and "pXL741" into an appropriate strain of *E. coli* such as *E. coli* 54125 (Pasteur Institute Collection), there are obtained strains producing, respectively, the hybrid proteins PAM1-HSA, PAM2-HSA and PAM3-HSA in proportions of the order of 5 to 10 mg/l of medium for an absorbance of 1 at 610 nm when operating under the conditions described in European Patent Application EP 86/400,618.4 (200,590).

The hybrid protein is found in the insoluble fraction of the cell lysate and can be renatured and partially purified using the previously described methods. Each hybrid protein obtained after renaturation may be converted into mature HSA by digestion conducted by means of an optimized concentration of trypsin under the previously described conditions.

In accordance with the provisions of the Budapest Treaty, the following deposits were made on Feb. 2nd 1987 at Centraalbureau voor Schimmelcultures (CBS) Oosterstraat I 3740 AG Baarn Netherlands:

A specimen of *Escherichia coli* E 103S (pRK248clts) containing the plasmid pXL 462 (strain G-1398) under No. CBS 143.87;

A specimen of *E. coli* B containing the plasmid pXL 641 (strain G-2083) under No. CBS 144.87;

A specimen of *E. coli* B containing the plasmid pXL 740 (strain G-2146) under No. CBS 145.87; and A specimen of *E. coli* B containing the plasmid pXL 741 (strain G-2147) under No. CBS 146.87.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. A hybrid protein comprising a peptide sequence of the first seven amino acids of the lambda bacteriophage cII protein, (Met)-Val-Arg-Ala-Asn-Lys-Arg, fused to the N-terminal end of the peptide sequence of mature human serum albumin, when produced by culture of a strain of *Escherichia coli* which ensures the maintenance of the plasmid "pXL462".

2. A hybrid protein comprising a peptide sequence of the first six amino acids of an N-terminal penicillin amidase which has been modified by directed mutagenesis, Met-Lys-Asn-Arg-Lys-Arg, fused to the N-terminal end of the peptide sequence of mature human serum albumin, when produced by culture of a strain of *Escherichia coli* which ensures the maintenance of the plasmid "pXL740".

3. A hybrid protein comprising a peptide sequence of the first six amino acids of a penicillin amidase which has been modified by directed mutagenesis, Met-Lys-Lys-Arg-Lys-Arg, fused to the N-terminal end of the peptide sequence of mature human serum albumin, when produced by culture of a strain of *Escherichia coli* which ensures the maintenance of the plasmid "pXL741".

4. A hybrid protein comprising a peptide sequence of the first six amino acids of the penicillin amidase, Met-Lys-Asn-Arg-Asn-Arg, fused to the N-terminal end of the peptide sequence of mature human serum albumin, when produced by culture of a strain of *Escherichia coli* which ensures the maintenance of the plasmid "pXL641".

* * * * *